United States Patent [19]

Broida

[11] Patent Number: 5,203,806
[45] Date of Patent: * Apr. 20, 1993

[54] ABSORBENT PAD FOR MEDICAL USE

[76] Inventor: Marna Broida, P.O. Box 1558, North Kingstown, R.I.

[*] Notice: The portion of the term of this patent subsequent to May 7, 2008 has been disclaimed.

[21] Appl. No.: 658,531

[22] Filed: Feb. 21, 1991

Related U.S. Application Data

[63] Continuation of Ser. No. 388,607, Aug. 2, 1989, Pat. No. 5,013,307.

[51] Int. Cl.⁵ ............................................. A61F 5/44
[52] U.S. Cl. .................................... 604/338; 604/332
[58] Field of Search ................ 604/338, 332, 333–337, 604/339–345, 358, 368, 386

[56] References Cited

U.S. PATENT DOCUMENTS

| | | | |
|---|---|---|---|
| 4,857,065 | 8/1989 | Seal | 604/368 |
| 4,865,594 | 9/1989 | Thomas | 604/332 |
| 4,886,509 | 12/1989 | Mattsson | 604/349 |
| 5,013,307 | 5/1991 | Broida | 604/338 |

*Primary Examiner*—Randy C. Shay
*Assistant Examiner*—Gina Gualtieri
*Attorney, Agent, or Firm*—Evelyn M. Sommer

[57] ABSTRACT

An absorbent pad for use with an ostomy appliance or similar apparatus connected to a stoma extending through the skin of a patient, is formed of a flexible laminate with a liquid-permeable inner layer facing toward the patient's skin, an intermediate layer of absorbent material, and a liquid-impermeable outer layer. The layers are sealed together, and the laminate has a central opening for fitting around the connection between the ostomy appliance flange and body portion. An adhesive layer is provided on the peripheral border of the pad for sealing to the patient's skin. The adhesive layer is applied so that it encircles the absorbent surface area of the pad. The adhesive layer cooperates with the impermeable outer layer of the laminate to surround the fluid-absorbing intermediate layers of the pad and prevent fluid and odor absorbed therein from being released. The absorbent pad is further characterized in that it can be applied and disposed of separate and apart from the ostomy appliance.

8 Claims, 3 Drawing Sheets

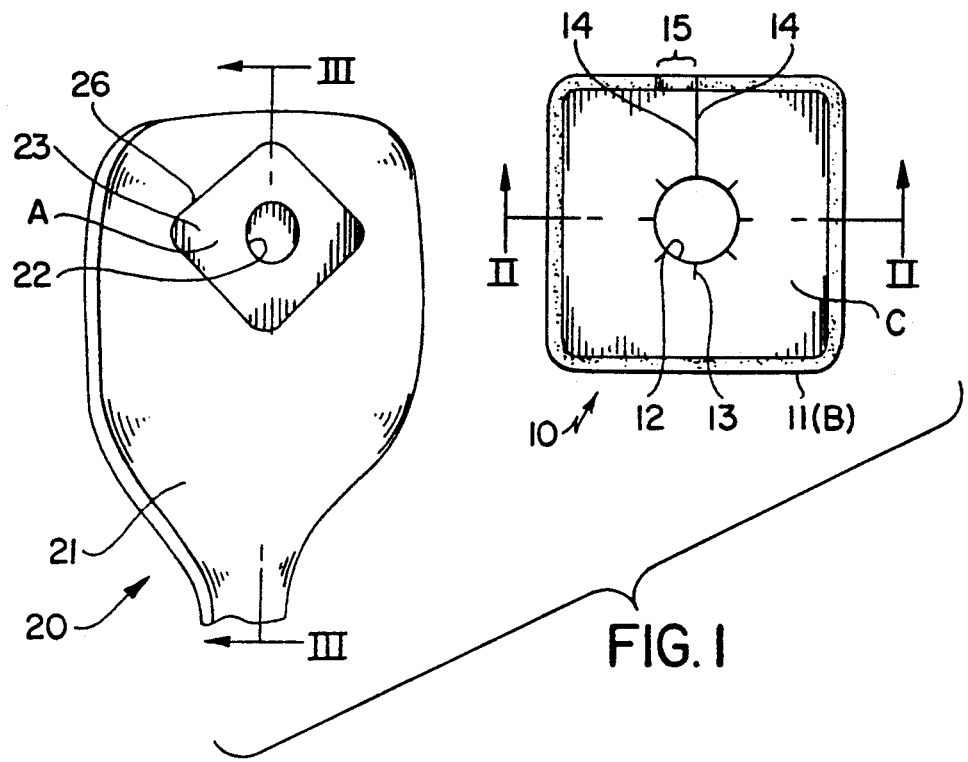
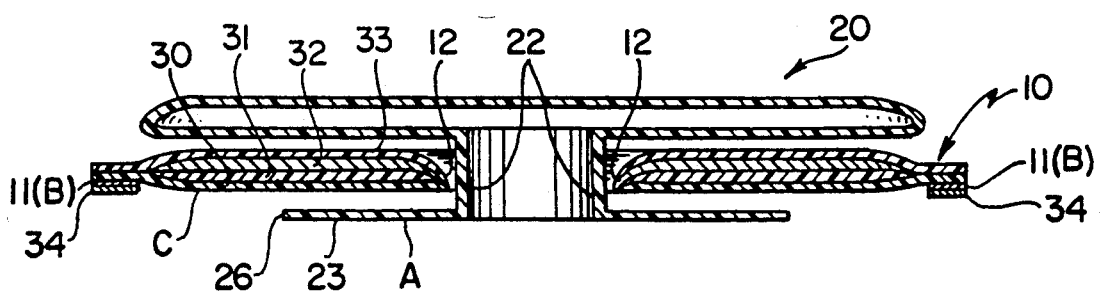

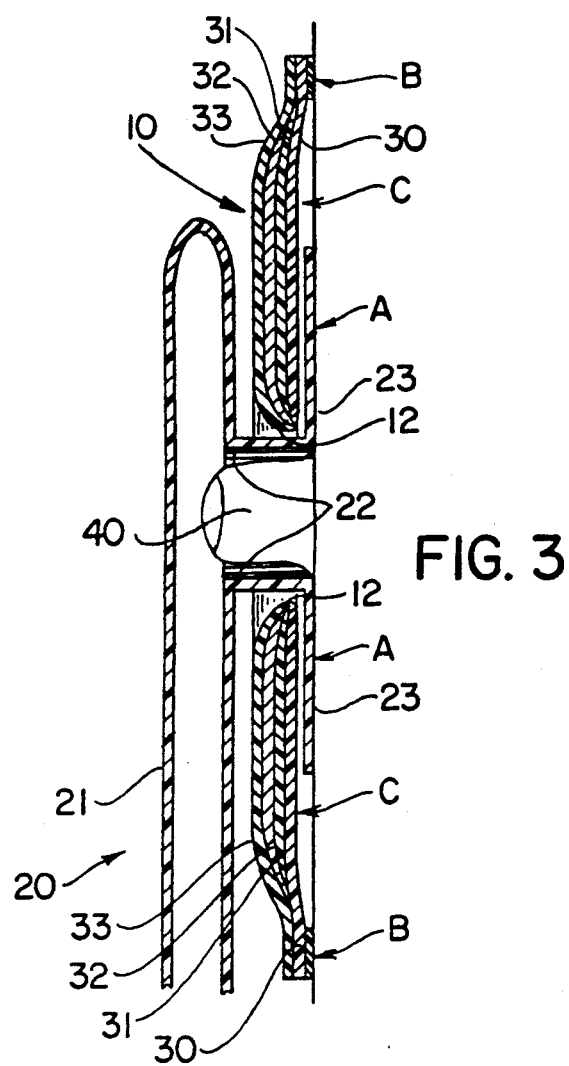
FIG. 3
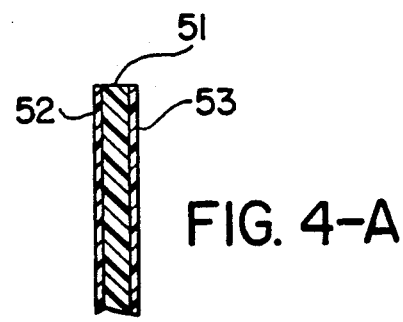
FIG. 4-A
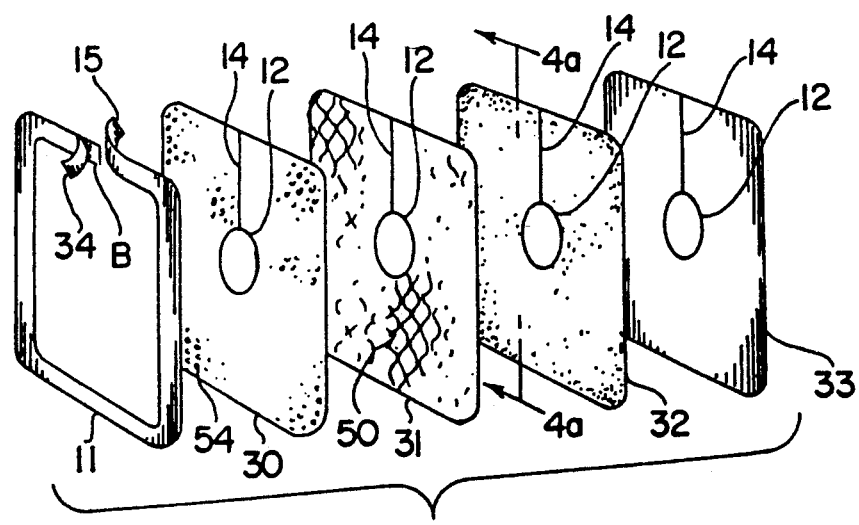
FIG. 4

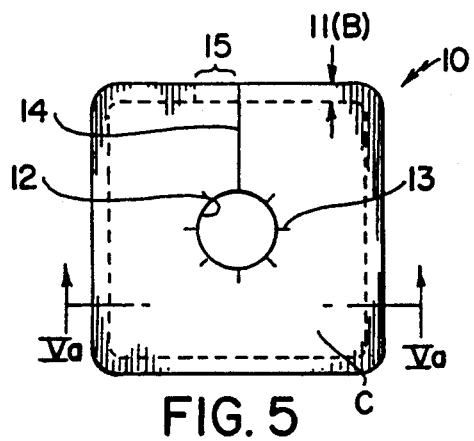
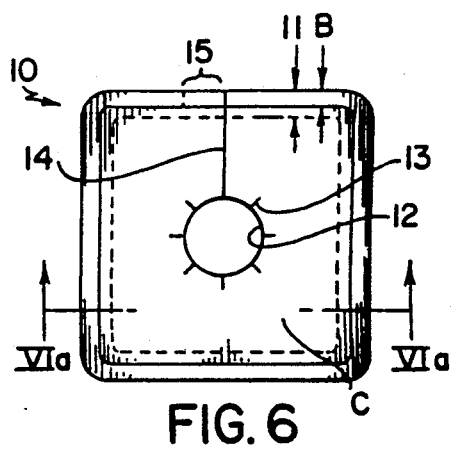
FIG. 5
FIG. 6
FIG. 5-A
FIG. 6-A
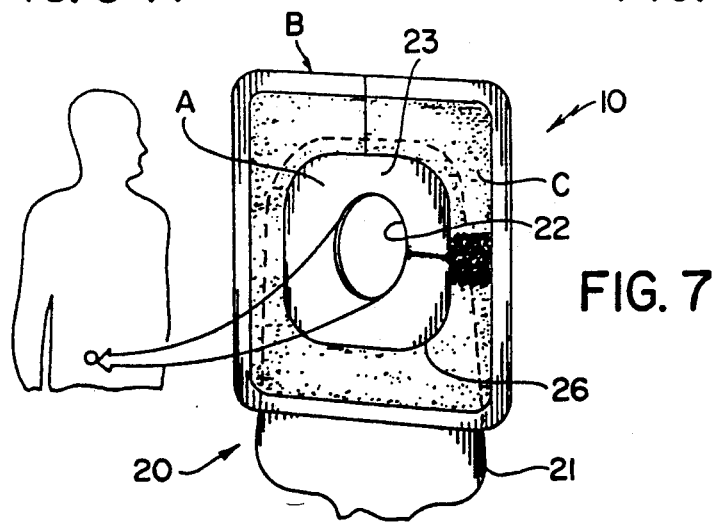
FIG. 7
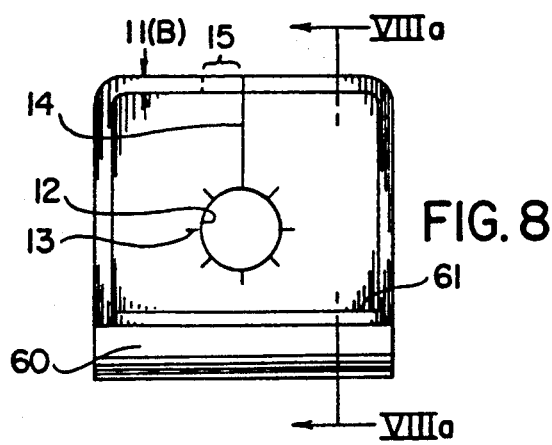
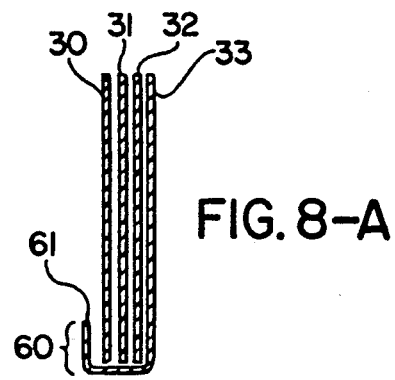
FIG. 8
FIG. 8-A

ABSORBENT PAD FOR MEDICAL USE

This application is a continuation of Ser. No. 388,607 filed Aug. 2, 1989, now U.S. Pat. No. 5,013,307.

FIELD OF THE INVENTION

This invention generally relates to an absorbent pad for medical use, and more particularly, to an absorbent pad designed for convenient use with an ostomy appliance such as a urostomy or colostomy bag or similar collecting apparatus, to absorb leakage of fluid on a patient's skin.

BACKGROUND ART

In urostomy, colostomy, ileostomy, tracheotomy, and other similar operations, part or all of a patient's bladder, intestine, or other internal organ is removed, and is replaced with a conduit for channeling body fluids or waste out of the patient's body via a stoma or tube. In the case of a colostomy, ileostomy or urostomy, body waste is collected by an external apparatus, usually attached to the patient's skin around the stoma or tube. For example, a conventional ostomy appliance is a relatively flat plastic bag having an aperture to receive the stoma, the bag usually being formed with a flange for fitting around the stoma and for being sealed to the skin of the abdomen with an adhesive layer.

The adhesive layer of the appliance flange will sometimes leak due to an imperfect seal. Such a break in the seal can be caused by abdominal folds, wrinkles in the flange when it is first applied, strenuous physical activity, humidity, or other stresses placed on the adhesive, including those arising from the inflexibility of the flange in the central region where the flange is connected to the bag. The leak can result in stains on the patient's clothing and embarrassing odors. It is often inconvenient or impossible for the patient to change the appliance before a leak becomes noticeable.

Various types of absorbent pads have been designed for absorbing such leakage, including a pad designed to fit around the aperture of the collecting appliance. For example, in U.S. Pat. No. 4,406,659, a removable U-shaped absorbent pad is mounted with an adhesive strip, or held in a pouch on the inner, or skin-facing, surface of the urostomy bag over the lower half of the receptacle flange receiving the stoma. In U.S. Pat. No. 4,085,752, an absorbent pad is formed by doubling over the absorbent layers and providing a slit and annular opening for fitting immediately around the stoma against the patient's skin and underneath the receptacle flange of a colostomy appliance.

The absorbent pad of U.S. Pat. No. 4,085,752 is first placed on the skin around the stoma, and the appliance flange is next positioned on top of the pad. A belt must then be used to hold the bag and pad in place. This type of absorbent ostomy pad can only be used with the small proportion of appliances that do not use adhesive on the flange as the means of attachment. The pad, it should be noted, can only be applied or removed at the same time as the appliance itself.

Further, in U.S. Pat. No. 4,085,752, the pad acts like a sponge releasing retained fluid and odor when pressure is applied thereto. There is no provision made for trapping liquid absorbed by the pad and preventing it from leaking out when the pad becomes saturated and pressure is applied thereto. This circumstance would occur any time the wearer bent forward from the waist.

In addition, there is the disadvantage that the skin in contact with a wet pad would remain wet and, over a sustained period, could become irritated and excoriated.

Accordingly, it is a principle object of the present invention to provide a separately disposable, self-adhering absorbent pad, for use with an ostomy appliance or other external collecting apparatus fitting around a stoma or tube extending from a patient, adapted so that fluid which is not passed into the appliance will be absorbed and retained by the pad without leakage of fluid or odor therefrom for prolonged periods of time.

Another object of the invention is to provide such a construction wherein the fluid which cannot be accommodated by the pad is not released onto the patient's skin or clothing.

Still another object is to provide an absorbent pad which can be conveniently applied around the aperture of a collecting appliance, can be adjustingly fitted thereon despite variations in the dimensions thereof, and will remain securely in position.

A further object of the invention is to provide an absorbent pad adapted to cover the entire flange of the ostomy appliance for providing 360 degrees of protection against appliance failure.

Yet a further object is to provide an absorbent pad which is a totally separate device from the appliance, which can be removed completely independently of the appliance, and which is not subject to the stresses applied to the appliance flange by the rigid appliance aperture to which the flange is directly attached.

Still another object of the invention is to provide an absorbent pad adapted to be worn on the outside of the appliance flange and which is suitable for use with substantially all ostomy appliances including those attached with adhesive or by means of a belt.

Still a further object of the present invention is to provide an auxilliary means contained within such a pad for trapping large amounts of liquid by converting the same into a gel.

Another object of the present invention is to provide a flexible absorbent pad of substantially reduced bulk, as compared to the presently disclosed pads, which will contain odor in addition to leakage and which will trap liquid out of contact with the patient's skin.

These and other objects and advantages of the invention will be appreciated from the following disclosure.

SUMMARY OF THE INVENTION

In accordance with the invention, a separately replaceable, self-adhering absorbent pad, for use in absorbing fluid and/or semi-solid leakage around the flange of an ostomy appliance, comprises a flexible laminate formed with an inner layer of material permeable to fluid and capable of absorbing fluid and odor disposed on one side facing toward the patient's skin, and an outer layer of material impermeable to fluid disposed thereon facing away from the patient's skin.

In a preferred embodiment, the absorbent pad comprises a multi-layered laminate having an innermost layer adjacent to the patient's skin which is permeable to fluid but not absorbent; at least one and preferably two intermediate layers of absorbent material superposed thereon; and an outer layer of material impermeable to fluid facing away from the patient's skin, superposed on said intermediate absorbent material layer or layers.

The layers of the separately replaceable, self-adhering absorbent pad are sealed together, either along the peripheral borders thereof or by applying a pattern of adhesive between each two adjacent layers, the adhesive not necessarily being restricted to the borders of the layers.

The thin, flexible pad of the invention is provided with a hypoallergenic adhesive layer applied on the peripheral border either on the inner side of the pad facing toward the patient's skin, on top of the inner permeable layer if the intermediate, absorbent layers are cut smaller, or beyond the edge of the laminate if all layers are cut to the same size. In the latter case the adhesive layer is preferably applied in the form of a tape having adhesive deposited thereon for effecting the sealing of the pad to the patient's skin. In either case, the objective is to wholly enclose the absorbent intermediate layers with an adhesive seal.

The hypoallergenic adhesive layer on the peripheral border of the laminate seals the pad to the patient's skin and cooperates with the impermeable outer layer of the laminate to enclose the fluid-absorbing surface area of the absorbent pad and prevent fluid and odor absorbed therein from being released. While in the preferred embodiment the adhesive layer is provided along the entire peripheral border, it should be understood that the pad will still offer varying degrees of protection if the adhesive layer is only provided along some portion of the border, or if it is separately provided, or if directions are given the user to apply their own adhesive to the peripheral border.

An opening is formed through the laminate at a central position in the surface area thereof for fitting around the appliance aperture where the adhesive appliance flange is joined to the bag portion. The opening in the pad is suitably dimensioned for achieving a snug or tight fit around the appliance aperture. A slit extends perpendicularly from the opening out to one lateral side of the pad. This slit provides the means for separately removing the pad.

In order to maintain the pad's absorbency and integrity at this slit portion, an adhesive tab is provided either separately or else formed as an overlapping extension of the adhesive tape present on the perimeter of the pad. The overlapping adhesive tab is formed by applying a hypoallergenic adhesive layer onto a flexible ribbon or tape. The ribbon or tape is then applied onto the pad in the region of the slit so that a portion of the adhesive tape extends to form an overlapping adhesive tab. It is understood that the entirety of the hypoallergenic adhesive layer may be applied by means of such ribbon or tape but this is not necessary or required.

In the case of a separate tab, a strip of tape or ribbon with appropriate adhesive is applied directly onto the pad to cover an area including the cut edge portions of the slit.

A further feature of the invention includes the use of a superabsorbent polymer (SAP) which traps large amounts of liquid by converting the same into a gel. In accordance with this feature of the invention, the SAP is incorporated into the intermediate layer or layers, preferably the outermost intermediate layer, being uniformly distributed throughout such layer. This SAP layer is formed by joining together two sheets of cellulose tissue material with the SAP sandwiched between them.

It has already been proposed to employ SAP in ostomy pads to convert fluid into gel. But in the known constructions, the polymer has been introduced in loose, free form throughout the absorbent layer, so that it can and does settle unevenly, leaving portions of the pad with no SAP at all. Another disadvantage of the loose SAP is 'gel block.' Gel block occurs when the SAP is distributed throughout the entire thickness of a wood pulp-derived pad. Liquid entering the pad is trapped by the SAP closest to the leak entry point, which swells and blocks additional liquid from reaching the unused portion of the pad. The result is a saturated inner surface, while the outer layers remain unused, in essence decreasing the pad's capacity. The inventor does not claim the SAP laminate per se as her invention, but rather it is claimed as a preferred feature thereof. An example of such a SAP laminate is Gelok 6000 S/D, and is preferred since it traps large amounts of fluid in gel form.

In accordance with a further feature of the invention, the central opening has a crimped or slitted annular edge for fitting adjustingly around the aperture of the appliance. It is also possible to provide perforated concentric rings around the central opening adapted for easy removal to enlarge the central opening as required for fitting adjustingly around the aperture of the appliance.

It has been observed that leaks often occur at the top of the ostomy appliance flange. The absorbent pad of U.S. Pat. No. 4,406,659 only covers the lower half of the flange, thus providing inadequate protection. The absorbent pad of the present invention is adapted to cover the entire flange of the ostomy appliance, thereby providing 360 degrees of protection against appliance failure.

It has been established that the construction of the pad of the invention prohibits odor, as well as leakage, from escaping and embarrassing the wearer. The construction of the invention provides a liquid- and odor-impermeable outer layer and an adhesive perimeter. If the ostomy appliance flange fails and a leak occurs that is large enough to saturate the pad, the pad of the invention will still be able to provide a barrier between the leakage and odor and the outside environment until the wearer can change both the pad and the faulty appliance.

The pads of the prior art do not include any means of attachment that would provide security to the wearer in the event that a leak occurs along an abdominal fold. If an ostomate has a horizontal crease that intersects the stoma, it becomes difficult to maintain a good seal between the abdomen and the adhesive flange of the appliance. The appliance adhesive will tend to pull away along the fold line. As a result, escaping liquid will travel inside the fold, past the pad and be absorbed by the wearer's clothing at the end of the fold.

The thin, flexible pad, as herein described, having a flexible band of adhesive around the entire perimeter thereof, is not attached to the appliance and therefore does not have the stresses applied to it that the conventional appliance flange adhesive has near the stiff central connection to a bag receptacle. Clinical data have shown that the pad of the present invention does adhere to irregularities in the skin in most cases, even in those instances where the ostomy appliance flange does not adhere. The pad therefore provides the wearer with the confidence of an effective barrier between the outside environment and the wetness and odor that accompany a leak.

Other objects, features, and advantages of the invention will become apparent from the detailed description of the preferred embodiment considered with the following drawings.

DESCRIPTION OF THE DRAWINGS

FIG. 1 is a perspective view of an absorbent pad in accordance with the invention for use with an ostomy appliance;

FIG. 2 is a cross-sectional view of one embodiment of the absorbent pad installed on an ostomy appliance taken along view line II—II in FIG. 1;

FIG. 3 is a cross-sectional view of an embodiment of the absorbent pad installed on an ostomy appliance taken along view line III—III in FIG. 1;

FIG. 4 shows an embodiment of the invention separated into its component parts;

FIG. 4-A is a cross-sectional view of the super absorbent polymer laminate layer of the absorbent pad taken along view line IVa—IVa in FIG. 4;

FIG. 5 is a front view of an embodiment of the absorbent pad showing one method of attaching the layers and placement of adhesive;

FIG. 5-A is a cross-sectional view of the embodiment in Fig. 5 taken along view line Va—Va;

FIG. 6 is a front view of an embodiment of the absorbent pad showing a second method of attaching the layers and placement of adhesive;

FIG. 6-A is a cross-sectional view of the embodiment of Fig. 6 taken along view line VIa—VIa;

FIG. 7 shows the method of operation of the absorbent pad, illustrating entrapment by the pad of leakage escaping from under the appliance flange;

FIG. 8 shows a further embodiment of the absorbent pad of the invention including a reservoir pouch; and FIG. 8-A is a cross-sectional view of the embodiment in Fig. 8 taken along view line VIIIa—VIIIa.

DESCRIPTION OF THE PREFERRED EMBODIMENTS

Referring to FIG. 1, an absorbent pad 10 in accordance with the invention has a fluid-absorbing side or core of a given surface area, generally designated "C", which, when installed, faces toward the skin of a patient. The size of the pad depends on its application, it being clear that a pad adapted for use with a colostomy appliance will have a surface area which is larger than that used for a tracheotomy. Generally, the pad's dimensions are less than ten inches on a side, and preferably five to nine inches on a side. It should also be understood that while the pad is described as being square or rectangular in shape, it could also be round or oval with no loss in suitability for its intended use.

In the embodiment of FIGS. 2 and 3, the pad 10 is a laminate of four layers including an absorbent core C comprised of layers 31, 32 and encircled by a liquid-impermeable peripheral border 11 so that the liquid absorbed in the pad's layers is contained within the sealed border 11. The pad has a significantly larger diameter than the adhesive flange 23 of the ostomy appliance in order to completely envelope the peripheral border 26 of the appliance flange.

On the inner skin-facing side of the peripheral border 11 is a hypoallergenic adhesive layer "B", to be described in further detail below, which is releasably adhered to the skin of the patient so as to completely surround the absorbent surface area C of the pad 10. A release tape or strip 34 (FIG. 2) initially protects, i.e. covers, the adhesive layer B before the pad is used. An opening 12 is formed through the pad 10 substantially in the center of its surface area to fit around the aperture 22 of the ostomy appliance attached to the patient.

The pad of the invention maximizes absorbency within a minimum space. In order for the pad to be as thin as possible, the layers in the embodiment, as shown in FIG. 4, each play a very specific role in the pad's overall function. First, the innermost layer 30, adjacent to the wearer's skin, allows fluid to pass through the tiny openings, or pores, 54. However, layer 30 itself is not absorbent. Therefore, even if the pad is saturated, the inner surface of the pad remains dry and comfortable to the touch, minimizing the chafing that could occur if moisture were held in contact with the skin over a long period of time.

The next succeeding layer 31, in the direction away from the wearer's skin, helps spread, or wick, liquid away from the leak entry point as quickly as possible so that the pad does not become saturated in one spot while the rest of the pad remains dry. This innermost intermediate layer 31 is similar to a sponge, having been embossed with channels 50 on its surface. The embossed layer 31 absorbs the fluid as it enters the pad and spreads the fluid as evenly as possible over the entire layer 31 via the series of interconnecting channels 50.

The next succeeding, or third, pad layer 32 in the direction away from the wearer's skin is the super absorbent Polymer (SAP) laminate. The laminate 32 is comprised of grains of SAP 51, sandwiched between two sheets of nonwoven cellulose tissue material 52, 53. The use of the laminate instead of the SAP in its free, unenclosed form, enables the pad to be extremely thin, as the SAP laminate can safely contain as much SAP as would normally be impregnated into the wood pulp of a pad many times as thick. The SAP laminate eliminates the need for bulky wood pulp which is costly to impregnate with SAP and to transport during fabrication. The SAP laminate 32 also virtually eliminates the problem of the SAP grains contacting the wearer's skin, as they are trapped behind the inner layers 30,31 of the Pad.

While the sponge-like embossed layer 31 spreads the leakage via the embossed channels 50, the SAP layer 32 draws the fluid out of the absorbent layer 31 and traps it in a gel form, as far as possible from the wearer's skin.

Finally, the outermost layer 33 of the pad is a fluid-impermeable barrier layer which acts to contain the liquid that is within the absorbent core C of the pad.

The permeable coverstock selected for layer 30 contains tiny openings, or pores 54, that allow liquid to pass through. The diameter of these pores is smaller than the diameter of the SAP grains 51. This provides an additional barrier between the grains of SAP and the wearer's skin, should any grains 51 shake free from the SAP laminate 32.

FIGS. 5, 5-A, 6 and 6-A illustrate two different means of sealing the layers of the absorbent pad together. In FIGS. 5 and 5-A, the innermost and outermost layers are sealed together along the peripheral borders thereof, enclosing therebetween the absorbent intermediate layers. The sealing can be accomplished by applying adhesive or heat and pressure around the perimeter in a conventional manner. In this instance, the innermost and outermost layers are slightly larger than the intermediate layer or layers, the latter being enclosed within the peripheral borders of the innermost and outermost layers.

In FIGS. 6 and 6-A, the layers as shown are all of substantially the same size and are sealed together by applying, as by printing, an adhesive in an appropriate pattern between each two adjoining layers. Alternatively, the sealing can be accomplished by applying heat and pressure in the indicated peripheral area. In this embodiment, for accomplishing the sealing to the patient's skin, a single-sided hypoallergenic adhesive tape is applied along the edge of the impermeable outer layer and extends past the edge to create an adhesive perimeter beyond the absorbent border.

In all embodiments, the hypoallergenic adhesive border extends beyond the absorbent surface area C of the pad so as to trap any fluid contained within the pad.

The absorbent pad 10 is used with an ostomy appliance 20, which typically has a sealed plastic body portion 21, an aperture 22 which fits around the stoma, and a flexible base plate or flange 23 with an adhesive layer "A" that is adhered to the patient's skin around the stoma (FIGS. 1 and 2). The opening 12 in the absorbent pad 10 is formed with a diameter for fitting snugly around the aperture 22. The pad 10 substantially completely overlaps the entire flange 23 of the ostomy appliance, including the peripheral border 26. In order to allow adjustment to variations in the sizes of the aperture 22, the pad's annular edge defining the opening 12 may be crimped or formed with slits 13 or may have perforated concentric rings (not shown) that may be popped out as needed to enlarge the opening 12.

A slit with cut edge portions 14 extends perpendicularly from the central opening 12 to one lateral side of the pad 10. The peripheral adhesive border 11 overlaps itself in the region of the slit to form a complete seal with an overlapping strip 15 having an adhesive on its inner side which adheres to the outer side of the peripheral border 11, thereby holding the cut edge portions 14 together. The use of an overlapping tab 15 is essential in maintaining the absorbent integrity of the pad 10, and preventing fluid from seeping out between the cut edge portions 14.

Referring to FIGS. 2, 3 and 4, the preferred absorbent pad is a laminate having a multi-layer structure, i.e. an inner or skin-facing layer 30 of material permeable to fluid which is placed in contact with the patient's skin, intermediate layers 31, 32 of absorbent material, and an outer layer 33 of material impermeable to fluid. The permeable inner layer 30 can be made of a nonwoven synthetic fiber material such as polyester or polypropylene which will not irritate the skin or retain fluids. The intermediate layer can be a combination of a nonwoven, lofted layer 31 made of cellulose fibers, and a conventional superabsorbent polymer laminate layer 32 comprised of a superabsorbent polymer 51 sandwiched between two sheets 52, 53 of non-woven material. Alternatively, layers 31, 32 can be combined as a single cellulosic layer impregnated with SAP.

A suitable example of a superabsorbent polymer laminate is made by Gelok International. Such superabsorbent materials typically are inert organic polymers which do not increase fluid volume, but can convert many times the particle weight of trapped fluid into a semi-solid gel. The impermeable outer layer 33 can be made of a polyethylene or other plastic film having impermeable properties.

In the case where the inner and intermediate layers are combined into a single absorbent layer, the superabsorbent polymer 51 is incorporated into this single layer predominantly toward the portion adjacent the outer layer 33 of fluid-impermeable material, in order to retain fluid and odors toward the side more remote from the patient's skin.

The use of the absorbent pad 10 with an ostomy appliance 20 will now be described with respect to the drawings. To install the pad 10, the cut edge portions 14 are held apart with the absorbent surface area C of the pad facing the patient's skin. The pad is drawn around the aperture 22 until the opposing cut edge portions 14 meet and the fluid absorbing side C of the pad substantially overlaps the entire peripheral border 26 of the flange 23.

It is advisable to remove the release tape 34 from the tab 15 to seal together the cut edge portions 14 before removing the release tape 34 from the entire adhesive perimeter of the pad. Whether attached or separately provided, the protective tape 34 is removed from the tab 15, and while the cut edge portions 14 are held together, the adhesive side of tab 15 is pressed directly over them forming a continuous unbroken border 11 around a continuous absorbent surface area C. Once the cut edge portions 14 are secured together, the release tape 34 is removed to expose the hypoallergenic adhesive layer B around the entire perimeter of the pad and the pad is pressed in place to adhere to the patient's skin.

As can be appreciated from FIG. 7, the absorbent surface area C of the pad 10 absorbs any fluid or waste material that fails to flow into the sealed plastic body portion 21 of the ostomy appliance 20 and instead works its way underneath the adhesive layer A on the flange 23 of the ostomy appliance, from the aperture 22 to the outer edge 26. The intermediate, absorbent layers 31, 32 of the pad 10 gradually fill with trapped fluid. However, because the adhesive layer B completely surrounds the absorbent surface area C and the outer layer 33 encloses the absorbent layers 31,32, no fluid or odor are released from the absorbent pad outwardly onto the patient's skin or clothing. The pad can be removed by releasing the adhesive layer B from the skin, and can be replaced with a new pad in the same manner as described above, with or without replacing the ostomy appliance 20.

A considerable advantage of the present invention is the ability to readily replace the pad even in situations where the appliance is not removed. It is not always convenient or possible to change the appliance when a leak occurs. For example, it takes up to 30 minutes to change an ostomy appliance. The ostomate may not have that much time, particularly if he is not in his own home. The wearer may also lack a proper place to dispose of the soiled bag There is also an additional cost associated with changing an appliance under sub-optimal conditions A change made under such circumstances can mean wasting an appliance on an emergency change only to have to later remove the fresh appliance to properly clean and dry the area around the stoma before replacing it with still another fresh appliance once back home. The situation can arise where the rate of leakage from around the outer edge 26 of the appliance flange 23 exceeds the ability of the pad's absorbent layers 31, 32 to absorb or spread the leakage to areas of the pad not yet saturated As shown in Fig. 8, a further embodiment of the invention provides for an integral reservoir pouch 60 arranged along the lowermost portion of the pad 10, dimensioned for containing only the lowermost portion of the pad. The uppermost edge portion 61 of the pouch 60 terminates substantially below the adhesive appliance flange 23 to ensure that the perimeter 26 of the adhesive appliance flange remains surrounded on all sides by the absorbent core C of the pad 10. The Pouch 60 Is formed of a flexible liquid impermeable material and preferably by folding over an extension of the outermost impermeable layer 33 of the pad The lower and side edges of the pouch 60 are joined together with the corresponding edge portions of the outermost impermeable layer 33 of the pad by means of adhesive or other conventional means.

The inwardly-directed reservoir pouch 60 is eminently adapted to receive any fluid not immediately absorbed by the pad 10. The fluid contained within the pouch can be absorbed by the intermediate layers 31, 32 of the pad 10 at such time as the rate of leakage decreases from around the perimeter 26 of the appliance flange 23. In the case where the pad cannot accommodate all of the fluid discharged, the pouch can serve as a receiving means until the pad and faulty appliance can be changed.

In order to assure secure attachment of the pad of this embodiment to the patient's skin, the releasable adhesive layer B is provided along the uppermost edge portion of the pouch facing toward the patient's skin. This ensures that the exposed absorbent core C of the pad is entirely surrounded by an adhesive perimeter.

From the foregoing description, it will be apparent to those skilled in the art that the present invention provides an improved absorbent pad for patients who have had urostomy, colostomy, ileostomy, or similar operations. The improved pad forms a seal against leakage of fluid and odor by completely surrounding the flange of the collecting appliance or apparatus and by its adhesive border completely surrounding the absorbent core. Thus, fluid and odor trapped in the pad are prevented from being released to outward areas of the patient's skin or clothing.

Numerous modifications are of course possible in light of the above disclosure. For example, although the preferred embodiment has a central opening for fitting around a flange of a collecting appliance, it may alternatively be formed with an opening that fits directly around the stoma or tube extending from the patient for use in other types of operations, such as tracheotomy. The shape, relative sizes, and materials may of course be changed without departing from the principles of the invention. It will be appreciated that other such modifications and variations of structures, products, and processes may be devised, all of which are considered to be within the spirit and scope of the invention as defined in the claims appended hereto.

The absorbent pad as described herein was produced in quantity and tested on ten subjects, each of whom had undergone ostomy surgery. The subjects were selected by nurses and pharmacists at hospitals and clinics in the New England region.

All subjects were interviewed before selection, to verify their ability to change their ostomy appliance unaided, and to communicate their thoughts and feelings. This was done to ensure that the subjects would be able to properly use and then convey their reactions to the absorbent pad of the invention.

Prior to this trial, the subjects wore only the standard ostomy appliance with no absorbent supplement, as no absorbent ostomy pad was/is conventionally or otherwise available to contain ostomy leakage and odor.

Each subject was provided with samples of the absorbent pad of the invention and instructed in the use thereof. Over a period of several months, the subjects were asked to wear the pads, and to complete the data sheets provided to them, recording: the dates the pads were worn; the times the pads were installed and removed; the times any leaks occurred, if they occurred while a pad was worn; and whether or not each pad contained the leak if a leak occurred during its use.

The subjects were also asked to compare, objectively and subjectively, the effects the pads had on their ability to function socially and professionally. The data were collected in written form and in taped interviews. The results of the foregoing trials are summarized in the table that follows.

Subject C had many physical ailments in addition to her ostomy, including several abscesses around the stoma. The abscesses caused drainage, unrelated to the stoma, underneath the seal of the appliance flange and of the absorbent pad. The result was that the pad did not adhere well and stoma leakage was not contained. After one unsuccessful test pad, this patient was removed from the trial.

The collected data and table establish that the pad was successful for eight of the nine remaining subjects. Subject I experienced only modest improvement in the containment of leakage and odor, and in his ability to function socially and at work. The explanation for the pad's limited success in this case was a very deep scar on the patient's abdomen that intersected the stoma. Through the entire trial period, 11 of the 13 pads that failed to contain the leakage were associated with Subject I. Including Subjects C and I, eighty-one percent (61/75) of the pads worn when a leak occurred succeeded in containing the leak. Excluding Subjects C and I, the success rate was 97 percent (56/58). The pad of the invention resulted in a marked improvement in the subjects' overall physical and emotional wellbeing.

| Patient | Sex | Age Range* | Type of Ostomy U = urostomy I = ileostomy C = colostomy | # Yrs. w/ Ostomy | Overall Physical Condition | # of Appliance Leaks While Wearing Pad | # Times Pad Contained Leak | Comments |
| --- | --- | --- | --- | --- | --- | --- | --- | --- |
| A | M | 46–60 | I | 36 | Excellent | 3 | 3 | Very satisfied |
| B | M | 46–60 | U | 8 | Poor | 2 | 2 | Very satisfied |
| C | F | 31–45 | U | 2 | Poor | 1 | 0 | Patient had abscesses adjacent to stoma which interfered w/ pad placement. Removed from trial after 1st pad. |
| D | F | 61–75 | U | 15 | Good | 10 | 10 | Very satisfied |
| E | M | 46–60 | C | 15 | Good | 3 | 3 | Very satisfied |
| F | F | 30 (approx.) | C | 14 | Moderate | 17 | 17 | Very satisfied |

-continued

CLINICAL TRIAL SUMMARY OF SUPERGUARD ABSORBENT OSTOMY PAD

| Patient | Sex | Age Range* | Type of Ostomy<br>U = urostomy<br>I = ileostomy<br>C = colostomy | # Yrs. w/ Ostomy | Overall Physical Condition | # of Appliance Leaks While Wearing Pad | # Times Pad Contained Leak | Comments |
|---------|-----|------------|------------------------------------------------------------------|------------------|----------------------------|----------------------------------------|----------------------------|----------|
| G | M | 61–75 | U | 23 | Good | 1 | 1 | Very satisfied |
| H | M | 31–45 | I | 2 | Excellent | 7 | 7 | Very satisfied |
| I | M | 61–75 | U | 8 | Poor | 16 | 5 | Patient has deep scar adjacent to stoma causing continuous leakage and necessitating an appliance change several times per day. |
| J | F | 17 (approx.) | U | 15 | Moderate | 15 | 13 | Very satisfied |

*Patients were asked to fill out a questionnaire indicating their age from a group of age ranges offered: 0–30, 31–45, 46–60, 61–75, 76–80, 80+.

I claim:

1. An absorbent pad for use with an ostomy appliance of the type having an enclosed bag portion and an adhesive flange which are connected together around an aperture adapted for receiving a stoma, to absorb fluid leakage from around the flange of said ostomy appliance, said absorbent pad comprising:

a flexible laminate formed with an inner layer of material permeable to and capable of absorbing fluid disposed on one side adapted to face toward a patient's skin and an outer layer of material impermeable to fluid disposed to cover said inner layer on an opposite side adapted to face away from the patient's skin, said layer being sealed together, and an opening formed through said laminate substantially in the center of said laminate being adapted for fitting securely around the connection between the ostomy appliance bag and flange enabling a peripheral edge of the ostomy appliance flange to terminate in a region that is surrounded by said inner layer.

2. An absorbent pad for use with an ostomy appliance of the type having an enclosed bag portion and an adhesive flange which are connected together around an aperture adapted for receiving a stoma, to absorb fluid leakage from around the flange of said ostomy appliance, said absorbent pad comprising:

a flexible laminate formed with an inner layer of material permeable to fluid disposed on one side adapted to face toward a patient's skin, at least one intermediate layer of material capable of absorbing fluid disposed on said inner layer, and an outer layer of material impermeable to fluid disposed to cover said inner and intermediate layers on an opposite side adapted to face away from the patient's skin, said layers being sealed together, and an opening formed through said laminate substantially in the center of said laminate being adapted for fitting securely around the connection between the ostomy appliance bag and flange enabling a peripheral edge of the ostomy appliance flange to terminate in a region that is surrounded by said inner layer.

3. An absorbent apparatus comprising an ostomy appliance having an enclosed body portion and an adhesive flange which are connected together around an aperture adapted for receiving a stoma, said flange being provided with an adhesive for adhering the flange to a patient's skin around the stoma, in combination with an absorbent pad according to claim 2.

4. An absorbent pad according to claim 2 in combination with means for securely holding said absorbent pad in close proximity to said patient's skin to prevent, in cooperation with said impermeable outer layer of said laminate, fluid from being released.

5. An absorbent pad according to claim 2, wherein said intermediate absorbent layer includes a superabsorbent polymer.

6. An absorbent pad according to claim 2 wherein, said intermediate absorbent layer includes a lofted layer of natural fibers.

7. An absorbent pad according to claim 2, further comprising a liquid impermeable reservoir pouch for containing a lowermost portion of said pad, an uppermost edge of said pouch terminating substantially below said appliance flange, said pouch being formed of a flexible liquid impermeable material, lower and side edges of said pouch being joined to similar edge portions of said outer layer to thereby form an inwardly directed pouch whereby any fluid not absorbed by said pad will be accomodated in the reservoir formed by said pouch.

8. An absorbent pad according to claim 7 in combination with means for securely holding said absorbent pad in close proximity to said patient's skin to prevent, in cooperation with said impermeable outer layer of said laminate, fluid from being released.

* * * * *